United States Patent
Carola et al.

(10) Patent No.: US 7,867,993 B2
(45) Date of Patent: Jan. 11, 2011

(54) PREPARATION CONTAINING OXIDIZED FLAVONOID DERIVATIVES

(75) Inventors: Christophe Carola, Heidelberg (DE); Sylvia Huber, Darmstadt (DE); Herwig Buchholz, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 140 days.

(21) Appl. No.: 11/719,712

(22) PCT Filed: Nov. 2, 2005

(86) PCT No.: PCT/EP2005/011687

§ 371 (c)(1),
(2), (4) Date: May 18, 2007

(87) PCT Pub. No.: WO2006/053637

PCT Pub. Date: May 26, 2006

(65) Prior Publication Data

US 2008/0319050 A1  Dec. 25, 2008

(51) Int. Cl.
*A01N 43/16* (2006.01)
*A61K 31/35* (2006.01)

(52) U.S. Cl. ...................... 514/183; 514/456
(58) Field of Classification Search ........................ None
See application file for complete search history.

(56) References Cited

FOREIGN PATENT DOCUMENTS

EP      0 774 249 A2 *  5/1997

OTHER PUBLICATIONS

Igarashi et al (Agricultural and Biological Chemistry 42(8):1617-1617, 1978) as evidenced by the attached CAPLUS Report.*
Pekkarinen et al (J Sci Food Agric 79:499-506, 1999).*
Mel'nikova et al (Chem of Natural Compounds 38:33-39, 2002).*
Utaka et al (J Chem Soc Commun 1824-1826, 1985).*
Ingarashi et al (Agric Biol Chem 42:1617-1619, 1978).*
Igarashi et al., An Oxidation Product of Quercetin Catalyzed By a Crude Enzyme Preparation from Red Clover (Trifolium Pratense L.); Its Isolation and Identification, Agric. Biol. Chem., 1990, 2143-2144, 54-8.
Igarashi et al., Aerial Oxidation Products of Quercetin in Acidic Solution, Agric. Biol. Chem., 1978, 1617-1719, 42-8.

* cited by examiner

*Primary Examiner*—Brandon J Fetterolf
*Assistant Examiner*—Craig Ricci
(74) *Attorney, Agent, or Firm*—Millen, White, Zelano & Branigan, P.C.

(57) ABSTRACT

The invention relates to novel compositions, in particular cosmetic and/or pharmaceutical compositions or food supplements, comprising at least one oxidized flavonoid derivative of the formula I, to novel oxidized flavonoid derivatives, and to novel uses of the oxidized flavonoid derivatives.

14 Claims, 2 Drawing Sheets

PREPARATION CONTAINING OXIDIZED FLAVONOID DERIVATIVES

The invention relates to novel compositions, in particular cosmetic and/or pharmaceutical compositions or food supplements, comprising at least one oxidised flavonoid derivative of the formula I, to novel oxidised flavonoid derivatives, and to novel uses of the oxidised flavonoid derivatives.

The human skin is subject to ageing processes, some of which are attributable to intrinsic processes (chrono-ageing) and some of which are attributable to exogenous factors (environmental, for example photo-ageing). In addition, temporary or even lasting changes to the skin picture may occur, such as, for example, acne, active or dry skin, keratoses, rosacea, light-sensitive, inflammatory, erythematosus, allergic or autoimmune-reactive reactions, such as dermatosis and photormatosis.

The exogenous factors include, in particular, sunlight or artificial radiation sources having a comparable spectrum, and compounds which can be formed by radiation, such as undefined reactive photoproducts, which may also be free-radical or ionic. These factors also include cigarette smoke and the reactive compounds present therein, such as ozone, free radicals, for example the hydroxyl free radical, singlet oxygen and other reactive oxygen and nitrogen compounds which interfere with the natural physiology or morphology of the skin.

Skin ageing is accompanied by a reduction in the layer thicknesses of the two skin layers, the epidermis and dermis, lying one on top of the other, and it is assumed that this is at least partly responsible for the formation of wrinkles in the ageing skin. While the epidermis, the upper layer, provides the skin in particular with resistance and forms the main barrier, the dermis, the lower layer, provides the skin with strength, elasticity and thickness. The epidermis consists principally of keratinocytes, which can be divided into four different differentiation stages. The epidermal differentiation is very important for the formation of the essential skin functions, namely as protective barrier against the environment and for the prevention of water loss from the body. In the final stage of epidermal differentiation, the cornified cell envelope is formed. Under the influence of transglutaminase, crosslinking of the proteins loricrin, small proline-rich proteins and involucrin occurs. Activation of the transglutaminase is therefore also a highly promising approach for improving the skin structure and combating skin ageing (anti-ageing).

The skin can be protected against exposure to light using cosmetic and/or pharmaceutical products which comprise UV filters. Particularly advantageous here are active compounds which, besides UV protection, also have an antioxidative action and thus protect the skin both by reducing the exposure to light and also by deactivation of free radicals induced by exposure to radiation or formed in another way.

Known antioxidants are flavonoids, which are frequently also used in dermatological compositions. However, it is disadvantageous that the flavonoids, owing to their low water solubility, can only be incorporated in comparatively small amounts into aqueous formulations of antioxidatively active compositions. Thus, for example, quercetin (cyanidanol, Cyanidenolon 1522, Meletin, Sophoretin, Ericin, 3,3',4',5,7-pentahydroxyflavone), which is frequently mentioned as a particularly effective antioxidant (for example C. A. Rice-Evans, N. J. Miller, G. Paganga, Trends in Plant Science 1997, 2(4), 152-159), has a solubility in water of only 0.04 g/l.

K. Lemanska, H. Szymusiak, B. Tyrakowska, R. Zielinski, A. E. M. F. Soffers, I. M. C. M. Rietjens; Free Radical Biology & Medicine 2001, 31(7), 869-881, are investigating the pH dependence of the antioxidative action of hydroxyflavones. Quercetin exhibits the highest activity of the investigated structures over the entire pH range.

The action of antioxidants is attributed to the fact that they can be oxidised more readily than the substances to be protected. If antioxidants are present, they are oxidised instead of the substances to be protected in the case of oxidative stress, so that the substances to be protected are not oxidised and are thus protected. However, the antioxidants are "consumed" as a consequence of their oxidation, meaning that they should be withdrawn from the composition with their (protective) function as antioxidants.

The object of the invention is to provide an antioxidatively active composition comprising at least one antioxidatively active compound having a high antioxidative efficacy, in which the active compound has adequately good solubility, so that it may be present in the composition in the concentration necessary for the strength of action desired in each case, and/or which has a protective action against UV rays and/or counters skin ageing.

Surprisingly, it has now been found that the compounds of the general formula I have a strong antioxidative action although they are the products of the oxidation of flavonoid derivatives and can be regarded, for example, as products of the oxidation of quercetin.

Owing to their antioxidative action, the compounds of the general formula I are eminently suitable as active compounds for antioxidatively active compositions, for example for those which counter skin ageing. The present invention therefore relates to an antioxidatively active composition comprising at least one compound of the general formula I

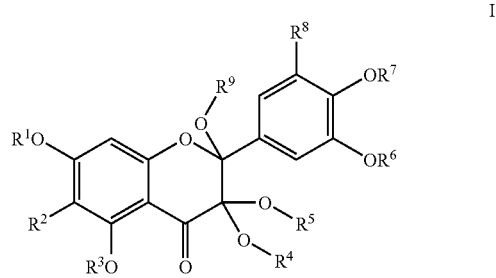

in which $R^1$, $R^3$, $R^4$, $R^5$, $R^6$, $R^7$, $R^9$ are each, independently of one another, H or alkyl and $R^2$, $R^8$ are each, independently of one another, H, OH or —O-alkyl, and optionally vehicles and/or assistants.

Alkyl in each case denotes straight-chain or branched $C_1$-$C_{10}$-alkyl having 1, 2, 3, 4, 5, 6, 7, 8, 9 or 10 carbon atoms and therefore preferably denotes methyl, ethyl, n-propyl, isopropyl, n-butyl, sec-butyl, tert-butyl, pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, heptyl, octyl, nonyl or decyl. Particular preference is given to $C_1$-$C_6$-alkyl, in particular butyl.

According to an advantageous embodiment of the invention, the composition comprises at least one compound of the formula I which is characterised in that $R^1$, $R^3$, $R^4$, $R^5$, $R^6$, $R^7$, $R^9$ are each, independently of one another, H, branched or straight-chain $C_1$-$C_6$-alkyl, preferably methyl, ethyl, n-propyl, n-butyl, and $R^2$ and $R^8$, independently of one another, are H or OH. In the compound of the formula I present in the composition according to the invention, preferably $R^4$=$R^5$.

According to a particularly advantageous embodiment of the invention, the composition comprises at least one compound of the formula I which is characterised in that $R^1$ to $R^8$ are each H, and $R^9$ is H or $C_{1-6}$-alkyl, in particular methyl, ethyl, n-propyl or n-butyl.

Oxidised flavonoid derivatives of the formula I in which $R^1$ to $R^8$ are each H and $R^9$ is methyl or ethyl are known from Agric. Biol. Chem. 54 (8), 2143-2144 (1990), where they were isolated from sun-dried red clover. The oxidised flavonoid derivatives correspond to oxidised quercetin, with the latter apparently being converted into the corresponding 2-O-methyl derivative, for example as a consequence of its work-up with methanol as extractant. The publication investigates the degradation of a nutrition-physiologically valuable red clover protein isolate which forms due to continuous exposure to sunlight. The authors conjecture that the damage to the amino acid residues which accompanies the protein degradation is caused by the oxidised flavonoid derivatives found. Thus, this paper reveals absolutely no teaching that the compounds have antioxidative properties and could therefore be used as antioxidants. On the contrary, the conjecture that the quercetin oxidation products contributed to the protein degradation directly discourages their use as antioxidants since antioxidants should after all prevent this very type of damage.

The compounds of the general formula I advantageously have significantly higher solubility in polar solvents, in particular in water, compared with the flavonoids known as antioxidants, such as, for example, quercetin, and can therefore be incorporated into the composition according to the invention in a simple manner and in a large amount. Mention may be made here by way of example of the solubility of the compound 2-butoxy-2-(3,4-dihydroxy-phenyl)-3,3,5,7-tetrahydroxychroman-4-one at 25° C. in water (2.9 g/l) and in ethanol (855 g/l). The solubilities of quercetin in water and in ethanol are, by contrast, only 0.04 g/l and 15.8 g/l respectively.

Furthermore, the compounds of the formula I absorb ultraviolet radiation in a very broad range. The compounds are therefore also particularly suitable for use as UV filters.

Advantages of the compositions according to the invention are, in particular, their antioxidative action and the good skin tolerability. In addition, the compounds described here are preferably colourless or have only a weak colour and thus only result in slight discoloration of the compositions, or none at all. Of particular advantage is the particular action profile of the compounds to be employed in accordance with the invention, which is evident in the DPPH assay from a high capacity to scavenge free radicals ($EC_{50}$), a delayed action ($T_{EC50}$>120 min) and thus a moderate to high anti-free-radical efficiency (AE). In addition, the compounds of the formula I combine antioxidative properties with UV absorption in the UV-A and/or UV-B region in the molecule.

2,2-Diphenyl-1-picrylhydrazyl (DPPH) assay: 2,2-diphenyl-1-picrylhydrazyl is a free radical which is stable in solution. The unpaired electron results in a strong absorption band at 515 nm, and the solution has a dark-violet colour. In the presence of a free-radical scavenger, the electron is paired, the absorption disappears, and the decoloration proceeds stoichiometrically taking into account the electrons taken up. The absorbance is measured in a photometer. The anti-free-radical property of the substance to be tested is determined by measuring the concentration at which 50% of the 2,2-diphenyl-1-picrylhydrazyl employed has reacted with the free-radical scavenger. This concentration is expressed as $EC_{50}$, a value which can be considered to be a property of the substance under the given measurement conditions. The substance investigated is compared with a standard (for example tocopherol). The $EC_{50}$ value here is a measure of the capacity of the respective compound to scavenge free radicals. The lower the $EC_{50}$ value, the higher the capacity to scavenge free radicals. For the purposes of this invention, the expression "a large or high capacity to scavenge free radicals" is used if the $EC_{50}$ value is lower than that of tocopherol.

The $T_{EC50}$ value (measured in minutes) is obtained from the time in which the $EC_{50}$ value is achieved and thus describes the rate at which these antioxidants scavenge free radicals. For the purposes of this invention, antioxidants which achieve this value within less than 60 minutes are regarded as fast, those which only achieve the $EC_{50}$ value after more than 120 minutes are regarded as having a delayed action.

The anti-free-radical efficiency (AE) (described in C. Sanchez-Moreno, J. A. Larrauri and F. Saura-Calixto in J. Sci. Food Agric. 1998, 76(2), 270-276) is given by the above-mentioned quantities in accordance with the following relationship:

$$AE = \frac{1}{EC_{50}T_{EC50}}.$$

A low AE ($\times 10^{-3}$) is in the range up to about 10, a morate AE is in the range from 10 to 20 and a high AE has in accordance with the invention values above 20.

The present invention therefore also relates to the use of the compounds of the formula I, as indicated above, as antioxidants having a long-lasting action or for the preparation of a composition having antioxidative properties.

A composition is taken to mean a formulation which comprises the compound of the formula I and is intended for use in humans or animals, for example by application to the skin, for oral ingestion, inhalation, infusion or injection. Depending on the type of composition, the composition may comprise vehicles and/or assistants in addition to a compound of the formula I, but it may also consist exclusively of the compound of the formula I itself for example in the form of a powder which can be, for example, taken directly orally or inhaled. Besides the compounds of the formula I, the composition may also comprise further active compounds.

The compositions here are usually pharmaceutical and/or cosmetic compositions, in particular compositions which can be used topically, for example cosmetic or dermatological formulations, or foods or food supplements. The compositions comprise a vehicle which is suitable for the particular type of composition and, depending on the desired property profile, optionally further suitable ingredients.

According to one embodiment, the composition according to the invention is characterised in that it is a pharmaceutical composition. At least one compound of the formula I is brought into a suitable dosage form here together with at least one solid, liquid and/or semi-liquid vehicle or assistant and optionally in combination with one or more further active compounds.

According to a preferred embodiment, the composition according to the invention is characterised in that it is a medicament.

The medicaments can be used in human or veterinary medicine. Suitable vehicles are organic or inorganic substances which are suitable for enteral (for example oral), parenteral or topical administration and do not react with the compounds of the formula I, for example water, vegetable oils, benzyl alcohols, alkylene glycols, polyethylene glycols, glycerol triacetate, gelatine, carbohydrates, such as lactose or starch, magnesium stearate, talc or Vaseline. Suitable for oral use are, in particular, tablets, pills, dragees, capsules, powders, granules, syrups, juices or drops, suitable for rectal use are suppositories, suitable for parenteral use are solutions, preferably oily or aqueous solutions, furthermore suspensions, emulsions or implants, and suitable for topical use are ointments, creams or powders. The plant extracts may also be lyophilised and the resultant lyophilisates used, for example, for the preparation of injection preparations. The compositions indicated may be sterilised and/or comprise assistants, such as lubricants, preservatives, stabilisers and/or wetting agents, emulsifiers, salts for modifying the osmotic pressure, buffer substances, dyes, flavours and/or a plurality of further active compounds, for example one or more vitamins.

The compounds of the formula I are generally preferably administered in doses of between about 1 and 500 mg, in particular between 5 and 100 mg, per dosage unit. The daily dose is preferably between about 0.02 and 10 mg/kg of body weight. However, the specific dose for each patient depends on a very wide variety of factors, for example on the efficacy of the specific compound employed, on the age, body weight, general state of health, sex, on the diet, on the time and method of administration, on the excretion rate, medicament combination and severity of the particular disease to which the therapy applies.

The pharmaceutical formulations comprising at least one compound of the formula I can be prepared with the aid of techniques which are well known to the person skilled in the art.

Particular preference is given to a composition which is characterised in that it is a skin-treatment composition.

A skin-treatment composition is a cosmetic, dermatological or pharmaceutical composition which is suitable for topical use. The composition typically comprises conventional skin-tolerated vehicles which have been tested in accordance with the application and optionally further assistants and active compounds.

Particular preference is therefore furthermore given to a composition which is characterised in that it is a cosmetic composition.

The compounds of the formula I increase the resistance of the skin to environmental influences, such as, for example, drying-out, counter skin ageing, result in an improvement in the skin structure, in particular in the formation of smooth skin, and have an antiinflammatory action. The invention therefore also relates to the use of the compounds of the formula I for the preparation of a pharmaceutical and/or cosmetic composition for increasing the resistance of the skin to environmental influences, in particular drying-out, for preventing skin ageing, for improving the skin structure, in particular for the formation of smooth skin.

The compounds of the formula I also act as free-radical scavengers and thus counter oxidative stress. They furthermore have an anti-allergic and anti-irritative action and can thus be used for the treatment or preventative treatment of allergies, inflammation and irritation, in particular of the skin. The invention therefore also relates to the use of the compounds of the formula I for the preparation of a pharmaceutical and/or cosmetic composition for protection against oxidative stress and for combating allergies, inflammation and/or irritation. Preference is given to compositions for topical use on the skin.

In order that the compounds of the formula I are able to develop their positive action as free-radical scavengers on the skin particularly well, it may be preferred to allow the compounds of the formula I to penetrate into deeper skin layers. If the penetration depth into epidermal layers is inadequate, this can be increased by means of suitable transport agents, for example liposomes, which facilitate transport of the compound through the outer skin layers. Finally, systemic transport of the compounds of the formula I is also conceivable. The composition is then designed, for example, in such a way that it is suitable for oral administration.

In general, the substances of the formula I act as free-radical scavengers. Free radicals of this type are not only produced by sunlight, but are also formed under various conditions. Examples are anoxia, which blocks the flow of electrons upstream of the cytochrome oxidases and causes the formation of superoxide free-radical anions; inflammation associated, inter alia, with the formation of superoxide anions by the membrane NADPH oxidase of the leukocytes, but also associated with the formation (through disproportionation in the presence of iron(II) ions) of the hydroxyl free radicals and other reactive species which are normally involved in the phenomenon of phagocytosis; and lipid autoxidation, which is generally initiated by a hydroxyl free radical and produces lipidic alkoxy free radicals and hydroperoxides.

Owing to their actions, the compounds of the formula I are also suitable for the preparation of compositions for immune protection and for the protection of DNA and RNA. In particular, the compositions obtained are suitable for the protection of DNA and RNA against oxidative attack, against free radicals and against damage due to radiation, in particular UV radiation. If the compounds are used in the form of compositions for use on the skin, a double protective action against UV radiation arises: through absorption of UV radiation, which prevents it acting on the skin, and through the action as free-radical scavenger, which counters the free radicals induced by UV radiation nevertheless penetrating.

It is assumed that the preferred compounds of the formula I also act as enzyme inhibitors. They presumably inhibit histidine decarboxylase, protein kinases, elastase, aldose reductase and hyaluronidase, and therefore enable the intactness of the basic substance of vascular sheaths to be maintained. Furthermore, they presumably inhibit non-specifically catechol O-methyl transferase, causing the amount of available catecholamines and thus the vascular strength to be increased. Furthermore, they inhibit AMP phosphodiesterase, giving the substances potential for inhibiting thrombocyte aggregation.

Owing to these properties, the compositions according to the invention are, in general, suitable for immune protection and for the protection of DNA and RNA. In particular, the compositions are suitable for the protection of DNA and RNA against oxidative attack, against free radicals and against damage due to radiation, in particular UV radiation. A further advantage of the compositions according to the invention is cell protection, in particular protection of Langerhans cells against damage due to the above-mentioned influences. All these uses and the use of the compounds of the formula I for the preparation of compositions which can be employed correspondingly are expressly also a subject-matter of the present invention.

In particular, preferred compositions according to the invention are also suitable for the treatment of skin diseases associated with a defect in keratinisation which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other defects in keratinisation, in particular ichthyosis, ichthyosiform states, Darier's disease, keratosis palmoplantaris, leukoplakia, leukoplakiform states, herpes of the skin and mucous membrane (buccal) (lichen), for the treatment of other skin diseases associated with a defect in keratinisation and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, it furthermore being possible for the compounds to be used for some inflammation which is not associated with a defect in keratinisation, for the treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma basocellulare and epithelioma spinocellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophy of the epidermis and/or dermis caused by locally or systemically applied corticosteroids and all other types of skin atrophy, for the prevention or treatment of defects in wound healing, for the prevention or elimination of stretch marks caused by pregnancy or for the promotion of wound healing, for combating defects in sebum production, such as hyperseborrhoea in acne or simple seborrhoea, for combating or preventing cancer-like states or pre-carcinogenic states, in particular promyelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and non-insulin-dependent diabetes, for the treatment of skin problems caused by UV radiation.

The present application therefore furthermore relates to a composition for topical use comprising
  a) at least one compound of the formula I, as described above,
  b) a skin-tolerated vehicle, and
  c) optionally one or more further active compounds having a skin-care and/or inflammation-inhibiting action.

In a preferred embodiment of the present invention, the composition is therefore a composition for the protection of body cells against oxidative stress, in particular for reducing skin ageing, characterised in that it preferably comprises one or more further antioxidants besides one or more compounds of the formula I.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to µmol/kg), and also (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylidene-glucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Mixtures of antioxidants are likewise suitable for use in the topical compositions according to the invention. Known and commercial mixtures are, for example, mixtures comprising, as active compounds, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed with compounds of the formula I in such compositions in ratios in the range from 1000:1 to 1:1000, preferably in amounts of 100:1 to 1:100.

It may be particularly preferred in accordance with the invention to combine fast-acting antioxidants with those having a slow or delayed action. Typical weight ratios of the fast-acting antioxidants to delayed-action antioxidants here are in the range 10:1 to 1:10, preferably in the range 10:1 to 1:1 and for skin-protecting compositions particularly preferably in the range 5:1 to 2:1. In other compositions which are likewise preferred in accordance with the invention, it may, however, be advantageous for the purposes of action optimisation for more delayed-action antioxidants to be present than fast-acting antioxidants. Typical compositions then exhibit weight ratios of the fast-acting antioxidants to delayed-action antioxidants in the range 1:1 to 1:10, preferably in the range 1:2 to 1:8.

The protective action against oxidative stress or against the action of free radicals can thus be further improved if the compositions comprise one or more further antioxidant(s), where the person skilled in the art is presented with absolutely no difficulties in selecting suitably fast-acting or delayed-action antioxidants.

The compositions according to the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin B), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active compound), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin. Vitamins are usually employed here with compounds of the formula I in ratios in the range from 1000:1 to 1:1000, preferably in amounts of 100:1 to 1:100.

Owing, inter alia, to the antioxidative action of the compounds of the formula I, they are also suitable for the protection of human skin or for the protection of body cells against oxidative stress, i.e., for example, against damage caused by free radicals, as are produced by exposure to sunlight. The protection against ultraviolet radiation by the composition according to the invention can be increased further by incorporation of one or more further UV filter(s).

In addition, preferred compounds of this type have advantages on incorporation into the compositions:
if $R^1$, $R^3$, $R^4$, $R^5$, $R^6$, $R^7$ and/or $R^9$=H and/or $R^2$ and/or $R^8$=OH, this improves the water solubility of the compounds to be employed in accordance with the invention;
if $R^1$, $R^3$, $R^4$, $R^5$, $R^6$, $R^7$ and/or $R^9$ are straight-chain or branched $C_1$ to $C_{10}$-alkyl groups, in particular a long-chain alkyl group, and/or $R^2$ and/or $R^8$=H, this increases the oil solubility of the compounds;

i.e. the hydrophilicity or lipophilicity of the compounds according to the invention can be controlled via a suitable choice of the substituents.

In likewise preferred embodiments of the invention, the compounds of the general formula I may also be present in the composition matrix in an amount going beyond their solubility. In this case, the compounds are preferably dispersed in finely divided form in the composition.

Compositions which are particularly preferred in accordance with the invention also comprise pure UV filters in addition to the compounds of the formula I.

The invention therefore furthermore relates to a composition comprising one or more compound(s) of the formula I which is characterised in that it furthermore comprises one or more UV filters.

In principle, all UV filters are suitable for combination with the compounds of the formula I according to the invention. Particular preference is given to UV filters whose physiological acceptability has already been demonstrated. Both for UV-A and UV-B filters, there are many proven substances known from the specialist literature, for example benzylidenecamphor derivatives, such as
   3-(4'-methylbenzylidene)-dl-camphor (for example Eusolex® 6300),
   3-benzylidenecamphor (for example Mexoryl® SD),
   polymers of N-{(2 and 4)-[(2-oxoborn-3-ylidene)methyl] benzyl}acrylamide (for example Mexoryl® SW),
   N,N,N-trimethyl-4-(2-oxoborn-3-ylidenemethyl) anilinium methylsulfate (for example Mexoryl® SK) or
   α-(2-oxoborn-3-ylidene)toluene-4-sulfonic acid (for example Mexoryl® SL), benzoyl- or dibenzoylmethanes, such as
   1-(4-tert-butylphenyl)-3-(4-methoxyphenyl)propane-1,3-dione (for example Eusolex® 9020) or
   4-isopropyldibenzoylmethane (for example Eusolex® 8020), benzophenones, such as
   2-hydroxy-4-methoxybenzophenone (for example Eusolex® 4360) or
   2-hydroxy-4-methoxybenzophenone-5-sulfonic acid and its sodium salt (for example Uvinul® MS-40), methoxycinnamic acid esters, such as
   octyl methoxycinnamate (for example Eusolex® 2292) or
   isopentyl 4-methoxycinnamate, for example as a mixture of the isomers (for example Neo Heliopan® E 1000), salicylate derivatives, such as
   2-ethylhexyl salicylate (for example Eusolex® OS),
   4-isopropylbenzyl salicylate (for example Megasol®) or
   3,3,5-trimethylcyclohexyl salicylate (for example Eusolex® HMS), 4-aminobenzoic acid and derivatives, such as
   4-aminobenzoic acid,
   2-ethylhexyl 4-(dimethylamino)benzoate (for example Eusolex® 6007) or
   ethoxylated ethyl 4-aminobenzoate (for example Uvinul® P25), benzimidazole derivatives, such as
   2-phenylbenzimidazole-5-sulfonic acid and potassium, sodium and triethanolamine salts thereof (for example Eusolex® 232),
   2,2'-(1,4-phenylene)bis(1H-benzimidazole-4,6-disulfonic acid, monosodium salt) (CAS No. 180 898-37-7) or
   2,2'-(1,4-phenylene)bis(1H-benzimidazole-5-sulfonic acid) and potassium, sodium and triethanolamine salts thereof, and further substances, such as
   2-ethylhexyl 2-cyano-3,3-diphenylacrylate (for example Eusolex® OCR),
   3,3'-(1,4-phenylenedimethylene)bis(7,7-dimethyl-2-oxo-bicyclo[2.2.1]-hept-1-ylmethanesulfonic acid and salts thereof (for example Mexoryl® SX),
   2,4,6-trianilino-(p-carbo-2'-ethylhexyl-1'-oxy)-1,3,5-triazine (for example Uvinul® T 150),
   2-(2H-benzotriazol-2-yl)-4-methyl-6-(2-methyl-3-(1,3,3,3-tetramethyl-1-(trimethylsilyloxy)disiloxanyl)propyl) phenol (for example Silatrizole®),
   2-ethylhexyl 4,4'-[(6-[4-((1,1-dimethylethyl)aminocarbo-nyl)phenylamino]-1,3,5-triazine-2,4-diyl)diimino]bis (benzoate) (for example Uvasorb® HEB),
   α-(trimethylsilyl)-ω-[trimethylsilyl)oxy]poly[oxy(dim-ethyl [and about 6% of methyl[2-[p-[2,2-bis(ethoxycar-bonyl)vinyl]phenoxy]-1-methyleneethyl] and about 1.5% of methyl[3-[p-[2,2-bis(ethoxycarbonyl)vinyl) phenoxy)-propenyl] and 0.1 to 0.4% of (methylhydro-gen)silylene]] (n≈60) (CAS No. 207 574-74-1) or
   2,2'-methylenebis(6-(2H-benzotriazol-2-yl)-4-(1,1,3,3-tetramethylbutyl)-phenol) (CAS No. 103 597-45-1),
   2,4-bis{[4-(2-ethylhexyloxy)-2-hydroxyl]phenyl}-6-(4-methoxyphenyl)-1,3,5-triazine (CAS No. 103 597-45-, 187 393-00-6).

The compounds mentioned in the list should only be regarded as examples. It is of course also possible to use other UV filters.

These organic UV filters are generally incorporated into cosmetic formulations in an amount of 0.5 to 10% by weight, preferably 1-8% by weight.

Further suitable UV filters are also methoxyflavones corresponding to the earlier German patent application DE 10232595.2.

Organic UV filters are generally incorporated into cosmetic formulations in an amount of 0.5 to 20% by weight, preferably 1 to 15% by weight.

Conceivable inorganic UV filters are those from the group of the titanium dioxides, such as, for example, coated titanium dioxide (for example Eusolex® T-2000, Eusolex® T-AQUA), zinc oxides (for example Sachtotec®), iron oxides or also cerium oxides. These inorganic UV filters are generally incorporated into cosmetic compositions in an amount of 0.5 to 20% by weight, preferably 2 to 10% by weight.

If different inorganic or organic UV filters are employed, these can be used in virtually any desired ratios to one another. The ratios of the individual substances to one another are usually in the range 1:10-10:1, preferably in the range 1:5-5:1 and particularly preferably in the range 1:2-2:1. If UV-A and UV-B filters are employed, it is advantageous for most applications for the proportion of UV-B filters to predominate and the ratio of UV-A filters:UV-B filters to be in the range 1:1 to 1:10.

Preferred compounds having UV-filtering properties which may preferably be present in the composition according to the invention, in particular if this is a cosmetic composition, are 3-(4'-methylbenzylidene)-dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)-benzoate, 2-ethylhexyl 2-cyano-3,3-diphenylacrylate, 2-phenylbenzimidazole-5-sulfonic acid and potassium, sodium and triethanolamine salts thereof.

Combination of one or more compounds of the formula I with further UV filters enables the protective action against the harmful effects of UV radiation to be optimised.

Optimised compositions may comprise, for example, the combination of the organic UV filters 4'-methoxy-6-hydroxyflavone with 1-(4-tert-butylphenyl)-3-(4-methoxyphenyl)propane-1,3-dione and 3-(4'-methylbenzylidene)-dicamphor. This combination gives rise to broad-band protection, which can be supplemented by the addition of inorganic UV filters, such as titanium dioxide microparticles.

All the said UV filters can also be employed in encapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables preparation problems caused by the interaction of individual composition constituents with one another, such as crystallisation processes, precipitation and agglomerate formation, to be avoided since the interaction is suppressed.

It is therefore preferred in accordance with the invention for one or more of the above-mentioned UV filters to be in encapsulated form. It is advantageous here for the capsules to be so small that they cannot be viewed with the naked eye. In order to achieve the above-mentioned effects, it is furthermore necessary for the capsules to be sufficiently stable and the encapsulated active compound (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules which can particularly preferably be employed in accordance with the invention have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules in compositions according to the invention are preferably present in amounts which ensure that the encapsulated UV filters are present in the composition in the above-indicated amounts.

The invention therefore also relates to a composition which is characterised in that it furthermore comprises one or more UV filters.

The compositions according to the invention may in addition comprise further conventional skin-protecting or skin-care active compounds. These may in principle be any active compounds known to the person skilled in the art.

Particularly preferred active compounds are pyrimidinecarboxylic acids and/or aryl oximes.

Pyrimidinecarboxylic acids occur in halophilic microorganisms and play a role in osmoregulation of these organisms (E. A. Galinski et al., Eur. J. Biochem., 149 (1985) pages 135-139). Of the pyrimidinecarboxylic acids, particular mention should be made here of ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoine and ectoine derivatives, such as hydroxyectoine, can advantageously be used in medicaments. In particular, hydroxyectoine can be employed for the preparation of a medicament for the treatment of skin diseases. Other areas of application of hydroxyectoine and other ectoine derivatives are typically in areas in which, for example, trehalose is used as additive. Thus, ectoine derivatives, such as hydroxyectoine, can be used as protectant in dried yeast and bacterial cells.

Pharmaceutical products, such as non-glycosylated, pharmaceutical active peptides and proteins, for example t-PA, can also be protected with ectoine or its derivatives.

Of the cosmetic applications, particular mention should be made of the use of ectoine and ectoine derivatives for the care of aged, dry or irritated skin. Thus, European patent application EP-A-0 671 161 describes, in particular, that ectoine and hydroxyectoine are employed in cosmetic compositions, such as powders, soaps, surfactant-containing cleansing products, lip-sticks, rouge, make-ups, care creams and sunscreen preparations.

Preference is given here to the use of a pyrimidinecarboxylic acid of the formula

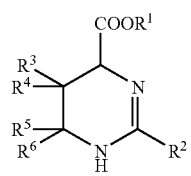

in which $R^1$ is a radical H or $C_{1-8}$-alkyl, $R^2$ is a radical H or $C_{1-4}$-alkyl, and $R^3$, $R^4$, $R^5$ and $R^6$ are each, independently of one another, a radical from the group H, OH, $NH_2$ and $C_{1-4}$-alkyl. Preference is given to the use of pyrimidinecarboxylic acids in which $R^2$ is a methyl or ethyl group, and $R^1$ or $R^5$ and $R^6$ are H. Particular preference is given to the use of the pyrimidinecarboxylic acids ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid). The compositions according to the invention preferably comprise pyrimidinecarboxylic acids of this type in amounts of up to 15% by weight. The pyrimidinecarboxylic acids are preferably employed here in ratios of 100:1 to 1:100 with respect to the compounds of the formula I, with ratios in the range 1:10 to 10:1 being particularly preferred. Of the aryl oximes, preference is given to the use of 2-hydroxy-5-methyllaurophenone oxime, which is also known as HMLO, LPO or F5. Its suitability for use in cosmetic compositions is disclosed, for example, in DE-A-41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and further allergic and/or inflammatory diseases of the skin and skin appendages. Compositions according to the invention which, in addition to the compound of the formula I, additionally comprise an aryl oxime, preferably 2-hydroxy-5-methyllaurophenone oxime, exhibit surprising antiinflammatory suitability. The compositions here preferably comprise 0.01 to 10% by weight of aryl oxime, it being particularly preferred for the composition to comprise 0.05 to 5% by weight of aryl oxime.

All compounds or components which can be used in the compositions are either known and commercially available or can be synthesised by known processes.

The one or more compounds of the formula I can be incorporated into cosmetic or dermatological compositions in the customary manner. Suitable compositions are those for external use, for example in the form of a cream, lotion, gel or as a solution which can be sprayed onto the skin. Suitable for internal use are administration forms such as capsules, dragees, powders, tablet solutions or solutions.

Examples which may be mentioned of application forms of the compositions according to the invention are: solutions, suspensions, emulsions, PIT emulsions, pastes, ointments, gels, creams, lotions, powders, soaps, surfactant-containing cleansing preparations, oils, aerosols and sprays. Examples of other application forms are sticks, shampoos and shower compositions. Any desired customary vehicles, assistants and, if desired, further active compounds may be added to the composition.

Preferred assistants originate from the group of the preservatives, antioxidants, stabilisers, solubilisers, vitamins, colorants, odour improvers, film formers and humectants.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary vehicles, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, mascara, eyeliner, eyeshadow, rouge, powder make-up, emulsion make-up and wax make-up, and sunscreen, pre-sun and after-sun preparations.

The preferred composition forms according to the invention include, in particular, emulsions.

Emulsions according to the invention are advantageous and comprise, for example, the said fats, oils, waxes and other fatty substances, as well as water and an emulsifier, as usually used for a composition of this type.

The lipid phase may advantageously be selected from the following group of substances:

mineral oils, mineral waxes;

oils, such as triglycerides of capric or caprylic acid, furthermore natural oils, such as, for example, castor oil;

fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;

silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of the esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of the esters of aromatic carboxylic acids and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of branched and unbranched hydrocarbons and waxes, silicone oils, dialkyl ethers, the group of the saturated or unsaturated, branched or unbranched alcohols, and fatty acid triglycerides, specifically the triglycerol esters of saturated and/or unsaturated, branched and/or unbranched alkanecarboxylic acids having a chain length of 8 to 24, in particular 12-18, C atoms. The fatty acid triglycerides may advantageously be selected, for example, from the group of the synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicaprylic ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane or poly(methylphenylsiloxane).

Also particularly advantageous are mixtures of cyclomethicone and isotridecyl isononanoate or cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984 or 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the compositions according to the invention comprise hydrophilic surfactants.

The hydrophilic surfactants are preferably selected from the group of the alkylglucosides, acyl lactylates, betaines and coconut amphoacetates.

The alkylglucosides are themselves advantageously selected from the group of the alkylglucosides which are distinguished by the structural formula

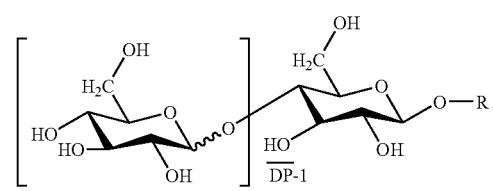

where R represents a branched or unbranched alkyl radical having 4 to 24 carbon atoms, and where $\overline{DP}$ denotes a mean degree of glucosylation of up to 2.

The value $\overline{DP}$ represents the degree of glucosidation of the alkylglucosides used in accordance with the invention and is defined as $$\overline{DP} = \frac{p_1}{100} \cdot 1 + \frac{p_2}{100} \cdot 2 + \frac{p_3}{100} \cdot 3 + \ldots = \sum \frac{p_i}{100} \cdot i$$

in which $p_1, p_2, p_3 \ldots p_i$ represent the proportion of mono-, di-, tri- ... i-fold glucosylated products in percent by weight. Advantageous in accordance with the invention is the selection of products having degrees of glucosylation of 1-2, particularly advantageously of 1.1 to 1.5, very particularly advantageously of 1.2 to 1.4, in particular of 1.3.

The value DP takes into account the fact that alkylglucosides are generally, as a consequence of their preparation, in the form of mixtures of mono- and oligoglucosides. A relatively high content of monoglucosides, typically in the order of 40-70% by weight, is advantageous in accordance with the invention.

Alkylglycosides which are particularly advantageously used in accordance with the invention are selected from the group octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and assistants or mixtures which are distinguished by an effective content of the active compounds used in accordance with the invention, for example Plantaren® 1200 (Henkel KGaA), Oramix® NS 10 (Seppic).

The acyllactylates are themselves advantageously selected from the group of the substances which are distinguished by the structural formula

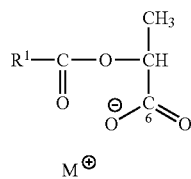

where $R^1$ denotes a branched or unbranched alkyl radical having 1 to 30 carbon atoms, and $M^+$ is selected from the group of the alkali metal ions and the group of ammonium ions which are substituted by one or more alkyl and/or one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group of the substances which are distinguished by the structural formula

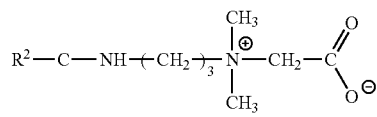

where $R^2$ denotes a branched or unbranched alkyl radical having 1 to 30 carbon atoms.

$R^2$ particularly advantageously denotes a branched or unbranched alkyl radical having 6 to 12 carbon atoms.

For example, capramidopropylbetaine, for example the product Tego® betaine 810 from Th. Goldschmidt AG, is advantageous.

A coconut amphoacetate which is advantageous in accordance with the invention is, for example, sodium coconut amphoacetate, as available under the name Miranol® Ultra C32 from Miranol Chemical Corp.

The compositions according to the invention are advantageously characterised in that the hydrophilic surfactant(s) is (are) present in concentrations of 0.01-20% by weight, preferably 0.05-10% by weight, particularly preferably 0.1-5% by weight, in each case based on the total weight of the composition.

For use, the cosmetic and dermatological compositions according to the invention are applied to the skin and/or the hair in an adequate amount in the usual manner for cosmetics.

Cosmetic and dermatological compositions according to the invention may exist in various forms. Thus, they may be, for example, a solution, a water-free composition, an emulsion or microemulsion of the water-in-oil (W/O) type or of the oil-in-water (O/W) type, a multiple emulsion, for example of the water-in-oil-in-water (W/O/W) type, a gel, a solid stick, an ointment or an aerosol. It is also advantageous to administer ectoines in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/N emulsions according to the invention.

Co-emulsifiers which are advantageous in accordance with the invention are, for example, O/W emulsifiers, principally from the group of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group of ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:

polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol (14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-14 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate/cocoate.

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Optional W/O emulsifiers, but ones which may nevertheless be advantageously employed in accordance with the invention are the following:

fatty alcohols having 8 to 30 carbon atoms, monoglycerol esters of saturated and/or unsaturated, branched and/or unbranched alkanecarboxylic acids having a chain length of 8 to 24, in particular 12-18 C atoms, diglycerol esters of saturated and/or unsaturated, branched and/or unbranched alkanecarboxylic acids having a chain length of 8 to 24, in particular 12-18 C atoms, monoglycerol ethers of saturated and/or unsaturated, branched and/or unbranched alcohols having a chain length of 8 to 24, in particular 12-18 C atoms, diglycerol ethers of saturated and/or unsaturated, branched and/or unbranched alcohols having a chain length of 8 to 24, in particular 12-18 C atoms, propylene glycol esters of saturated and/or unsaturated, branched and/or unbranched alkanecarboxylic acids having a chain length of 8 to 24, in particular 12-18 C atoms, and sorbitan esters of saturated and/or unsaturated, branched and/or unbranched alkanecarboxylic acids having a chain length of 8 to 24, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate, glyceryl monocaprylate.

The preferred compositions in accordance with the invention are particularly suitable for the protection of human skin against ageing processes and against oxidative stress, i.e. against damage caused by free radicals, as are produced, for example, by exposure to sunlight, heat or other influences. In this connection, they are in the various administration forms usually used for this application. For example, they may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants which are usually used in this type of composition, such as, for example, thickeners, softeners, moisturisers, surface-active agents, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk which, apart from the compound(s) of the formula I, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

The cosmetic composition may also be used to protect the hair against photochemical damage in order to prevent colour changes, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling and treating the hair, in the form of a lotion or gel for brushing or blow-waving, in the form of a hair lacquer, permanent waving composition, colorant or bleach for the hair. Besides the compound(s) of the formula I, the composition having light-protection properties may comprise various adjuvants used in this type of composition, such as surface-active agents, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

For the protection of the skin and/or natural or sensitised hair against sunlight, a cosmetic composition comprising at least one compound of the formula I is applied to the skin or the hair. Sensitised hair here is taken to mean hair which has been subjected to chemical treatment, such as permanent-wave treatment, or a colouring or bleaching process.

Furthermore, the compounds of the formula I also have a stabilising action on the formulation. On use in corresponding products, these therefore also remain stable for longer and do not change their appearance. In particular, the efficacy of the ingredients, for example vitamins, is retained even on extended use or extended storage. This is particularly advantageous in the case of compositions for the protection of the skin against the action of UV rays, since these cosmetics are subjected to particularly high stresses by the UV radiation.

The advantageous properties of the compounds of the formula I can also be utilised, for example, in their use in foods or as food supplements or as "functional food". For example, the compounds of the formula I can furthermore protect the compounds present in the food, the food supplement or the functional food and also the organism against oxidation or against the action of free radicals.

The invention therefore also relates to a food which is enriched with at least one compound of the formula I.

The invention furthermore relates to a food supplement which comprises at least one compound of the formula I. Food supplements are preferably compositions in the sense of the general definition given above and are preferably administered orally.

The further explanations given for foods also apply correspondingly to food supplements and functional food. The foods which can be enriched in accordance with the present invention with at least one compound of the formula I encompass all materials which are suitable for consumption by animals or for consumption by humans, for example vitamins and provitamins thereof, fats, minerals or amino acids. Foods which can be enriched in accordance with the present invention with compounds of the formula I are, for example, also foods which originate from a single natural source, such as, for example, sugar, unsweetened juice, squash or puree of a single plant species, such as, for example, unsweetened apple juice (for example also a mixture of different types of apple juice), grapefruit juice, orange juice, apple compote, apricot squash, tomato juice, tomato sauce, tomato puree, etc. Further examples of foods which can be enriched in accordance with the present invention with compounds of the formula I are corn or cereals from a single plant species and materials produced from plant species of this type, such as, for example, cereal syrup, rye flour, wheat flour or oat bran. Mixtures of foods of this type are also suitable for enrichment in accordance with the present invention with compounds of the formula I, for example multivitamin preparations, mineral mixtures or sweetened juice. As further examples of foods which can be enriched in accordance with the present invention with compounds of the formula I, mention may be made of food preparations, for example prepared cereals, biscuits, mixed drinks, foods prepared especially for children, such as yoghurt, diet foods, low-calorie foods or animal feeds.

The foods which can be enriched in accordance with the present invention with compounds of the formula I thus include all edible combinations of carbohydrates, lipids, proteins, inorganic elements, trace elements, vitamins, water and active metabolites of plants and animals.

The foods which can be enriched in accordance with the present invention with compounds of the formula I and the food supplements comprising at least one compound of the formula I are preferably administered orally, for example in the form of meals, pills, tablets, capsules, powders, syrups, solutions or suspensions.

As described, valuable cosmetic compositions, pharmaceutical compositions, foods and/or food supplements can be prepared by use/incorporation of compounds of the formula I in/into pharmaceutical and/or cosmetic compositions, foods and/or food supplements. The invention therefore also expressly relates to the use of the compounds of the formula I for the preparation of a cosmetic composition, a pharmaceutical composition, a food and/or a food supplement.

If the composition according to the invention comprises compounds of the formula I, this compound/these compounds is/are present in the following amounts, based on the composition as a whole:

in the case where the composition is a cosmetic and/or pharmaceutical formulation, in an amount of 0.001 to 100% by weight, preferably in an amount of 0.01 to 30% by weight, particularly preferably in an amount of 0.1 to 10% by weight in the case where the composition is a food, in an amount of 0.00001 to 20% by weight, preferably in an amount of 0.001 to 10% by weight, and in the case where the composition is a food supplement, preferably 0.1 to 80% by weight, based on the food supplement as a whole.

The foods enriched with compounds of the formula I can be prepared with the aid of techniques which are well known to the person skilled in the art.

Even without further comments, it is assumed that a person skilled in the art will be able to utilise the above description in the broadest scope. The preferred embodiments should therefore merely be regarded as descriptive disclosure which is absolutely not limiting in any way.

The complete disclosure content of all applications and publications mentioned above and below is incorporated into this application by way of reference.

The present invention furthermore relates to a process for the preparation of a composition, which is characterised in that at least one compound of the formula I containing radicals as described above is mixed with a vehicle which is suitable cosmetically or dermatologically or for foods, and to the use of a compound of the formula I for the preparation of a composition having antioxidative properties.

The compositions according to the invention can be prepared with the aid of techniques which are well known to the person skilled in the art.

The mixing can result in dissolution, emulsification or dispersion of the compound of the formula I in the vehicle.

The compounds of the formula I present in the composition according to the invention have, as described above, very advantageous properties. If the compounds have branched or straight-chain $C_3$-$C_{10}$-alkyl as $R^9$, they are also novel. Particular preference is given here to compounds in which $R^9$ is branched or straight-chain $C_3$-$C_{10}$-alkyl. The invention therefore also relates to a compound of the general formula I in which $R^9$ is branched or straight-chain $C_3$-$C_{10}$-alkyl, preferably branched or straight-chain $C_3$-$C_6$-alkyl.

Preference is given here to compounds of the formula I which are characterised in that $R^1$, $R^3$, $R^4$, $R^5$, $R^6$, $R^7$ are each, independently of one another, H, branched or straight-chain $C_1$-$C_6$-alkyl, preferably methyl, ethyl, n-propyl, n-butyl, and $R^2$ and $R^8$; independently of one another, are H or OH.

Particular preference is given to compounds of the formula I which are characterised in that $R^1$ to $R^8$ are each H.

Very particular preference is given to compounds of the formula I, as described above, which are characterised in that $R^9$ is n-propyl, isopropyl, n-butyl, sec-butyl or tert-butyl, n-pentyl, preferably n-propyl or n-butyl.

The compounds of the formula I can be prepared by dissolving or dispersing a compound of the general formula II

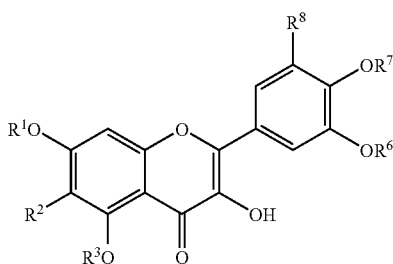

II in which $R^1$, $R^2$, $R^3$, $R^6$, $R^7$, $R^8$ have the same meanings as in the general formula I, in a monohydric alcohol $R^9$—OH, in which $R^9$ has the same meanings as in the general formula I, optionally adding a catalyst, bringing the compound of the formula II and the alcohol $R^9$—OH to reaction with one another with mixing and supply of oxygen, and subsequently isolating the resultant product.

The reaction of the compound of the formula II is preferably carried out in solution of the respective alcohol and in the presence of a catalyst, such as, for example, copper(II) chloride. The mixing is preferably carried out by stirring. The requisite reaction time, depending on the substituents of the formula II and the respective alcohol, is between 3 and 48 hours, typically between 12 and 24 hours. When the reaction is complete, the product is obtained, depending on the chain length of the alcohol, by removal by distillation, preferably, under reduced pressure, and if necessary crystallisation with an acid, such as, for example, hydrochloric acid, preferably 10% (w/w) hydrochloric acid, or by extraction.

The invention furthermore relates to a process for the preparation of the compound of the general formula I which is characterised by the steps described above.

The INCI names of the raw materials used are as follows (the INCI names are by definition given in English);

| Raw material | INCI name |
| --- | --- |
| Abil WE 09 | Polyglyceryl-4-Isostearate, Cetyl Dimethicone Copolyol, Hexyl Laurate |
| Antaron V-220 | PVP/Eicosene Copolymer |
| Arlacel 80 | Sorbitan Oleate |
| Arlacel 165 V | Glyceryl Stearate, PEG-100 Stearate |
| Avocado oil | *Persea Gratissima* |
| Beeswax | Beeswax |
| Biobase ™ EP | Glyceryl Stearate, Cetearyl Alcohol, Sodium Stearoyl Lactylate, Lecithin |
| Carbopol ETD 2050 | Carbomer |
| Cetiol V | Decyl Oleate |
| Cetyl alcohol | Cetyl Alcohol |
| Cetyl isononanoate | Cetyl Isononanoate |
| Cutina HR | Hydrogenated Castor Oil |
| Dimethicone | Dimethicone |
| Eusolex ® 232 | Phenylbenzimidazole Sulfonic Acid |
| Eusolex ® 2292 | Octyl Methoxycinnamate, BHT |
| Eusolex ® 6300 | 4-Methylbenzylidene Camphor |
| Eusolex 8300 | 4-Methylbenzylidene |
| Eusolex ® 9020 | Butyl Methoxydibenzoylmethane |
| Eusolex ® HMS | Homosalate |
| Eusolex T-Aqua | Aqua (Water), Titanium Dioxide, Alumina, Sodium Metaphosphate, Phenoxyethanol, Sodium Methylparaben |
| Eutanol G | Octyldodecanol |
| Germaben II | Propylene Glycol, Diazolidinyl Urea, Methylparaben, Propylparaben |
| Germaben II-E | Propylene Glycol, Diazolidinyl Urea, Methylparaben, Propylparaben |
| Glycerin | Glycerin |
| Glycerin (87%) | Glycerin |
| Glycerin (87% extra pure) | Glycerin |
| Glycerin, anhydrous | Glycerin |
| Hetester PHA | Propylene Glycol Isoceteth-3 Acetate |
| Hexyl laurate | Hexyl Laurate |
| Imwitor 960 K flakes | Glyceryl Stearate SE |
| Isolan PDI | Diisostearoyl Polyglyceryl-3-Diisostearat |
| Isopropyl myristate | Isopropyl Myristate |
| Isopropyl palmitate | Isopropyl Palmitate |
| Jojoba oil | *Buxus Chinensis* (Jojoba Oil) |
| Karion F liquid | Sorbitol |
| Keltrol RD | Xanthan Gum |
| Magnesium sulfate | Magnesium Sulfate |
| Magnesium sulfate heptahydrate | Magnesium Sulfate |
| Methyl 4-hydroxybenzoate | Methylparaben |
| Miglyol 812 | Caprylic/Capric Triglyceride |
| Miglyol 812 N | Caprylic/Capric Triglyceride |
| Miglyol 812, neutral oil | Caprylic/Capric Triglyceride |
| Mirasil CM5 | Cyclomethicone |
| Mirasil DM 350 | Dimethicone |
| Montanov 68 | Cetearyl Alcohol, Cetearyl Glucoside |

-continued

| Raw material | INCI name |
|---|---|
| Oxynex ® K | PEG-8, Tocopherol, Ascorbyl Palmitate, Ascorbic Acid, Citric Acid |
| Panthenol-D | Panthenol |
| Paracera M | Microwax |
| Paraffin oil, liq. | Mineral Oil |
| Perfume oil TND-2417 | Parfum |
| Pemulen TR-1 | Acrylates/$C_{10-30}$ Alkyl Acrylate Crosspolymer |
| Pemulen ® TR-2 | Acrylates/$C_{10-30}$ Alkyl Acrylate Crosspolymer |
| Performa ® V 825 | Synthetic Wax |
| Polyglyceryl 2-dipolyhydroxy-stearate | Polyglyceryl-2 Dipolyhydroxystearate |
| Prisorine 2021 | Isopropyl Isostearate |
| Propane-1,2-diol | Propylene Glycol |
| Propyl 4-hydroxybenzoate | Propylparaben |
| Rhodicare S | Xanthan Gum |
| RonaCare ™ ASC III | Aqua, Lecithin, Dipalmitoyl Hydroxyproline, Phenoxyethanol, Tall Oil Sterol, Linoleic Acid, Tocopherol, Sodium Ascorbate, Mannitol, Methylparaben, Ethylparaben, Propylparaben, Butylparaben |
| RonaCare ™ bisabolol | Bisabolol |
| RonaCare ™ ectoine | Ectoine |
| RonaCare ™ LPO | Lauryl p-Cresol Ketoxime |
| RonaCare ™ tocopherol acetate | Tocopheryl Acetate |
| Sepigel 305 | Polyacrylamide, $C_{13-14}$ Isoparaffin, Laureth-7 |
| SFE 839 | Cyclopentasiloxane, Dimethicone/Vinyldimethicone Crosspolymer |
| Shea butter | Shea Butter |
| Sodium chloride | Sodium Chloride |
| Sodium hydroxide solution, 10% | Sodium Hydroxide |
| Steareth-2 | Steareth-2 |
| Steareth-10 | Steareth-10 |
| Stearic acid | Stearic Acid |
| DL-α-Tocopherol acetate | Tocopherol Acetate |
| Triethanolamine | Triethanolamine |
| Triethanolamine extra pure | Triethanolamine |
| Water, demineralised | Aqua (Water) |
| Zinc stearate | Zinc Stearate |

The examples explain the invention without being restricted thereto.

EXAMPLE 1

Determination of the Antioxidative Action

The antioxidative action of the compounds of the formula I is investigated in a DPPH assay using the example of 2-butoxy-2-(3,4-dihydroxyphenyl)-3,3,5,7-tetrahydroxychroman-4-one. The comparative substance is quercetin, which has a very high antioxidative activity.

2,2-Diphenyl-1-picrylhydrazyl (DPPH) assay: 2,2-diphenyl-1-picrylhydrazyl is a free radical which is stable in solution. The unpaired electron results in a strong absorption band at 515 nm, the solution has a dark-violet colour. In the presence of a free-radical scavenger, the electron is paired, the absorption disappears, and the decoloration proceeds stoichiometrically taking into account the electrons taken up. The absorbance is measured in a photometer. In order to quantify the antioxidative action of the test substances, the $EC_{50}$ value is determined as the concentration of the test substance employed at which 50% of the 2,2-diphenyl-1-picrylhydrazyl employed has reacted therewith. The lower the $EC_{50}$ value, the higher the capacity to scavenge free radicals.

The DPPH assay is carried out by reaction of various concentrations of the test substances in ethanolic solution. Since the test substances react relatively slowly and the equilibrium states only become established relatively late, the determination of the $EC_{50}$ values is in each case based on the (absorbance) measurement values 600 minutes after commencement of the reaction. The $EC_{50}$ values are determined graphically.

For 2-butoxy-2-(3,4-dihydroxyphenyl)-3,3,5,7-tetrahydroxychroman-4-one, an $EC_{50}$ value of 0.08 is obtained, compared with an $EC_{50}$ value of 0.089 for quercetin. Surprisingly, the oxidised flavonoid according to the invention has a higher antioxidative activity than quercetin, which is regarded as a very strong antioxidant.

EXAMPLE 2

Preparation of 2-ethoxy-2-(3,4-dihydroxyphenyl)-3,3,5,7-tetrahydroxychroman-4-one 3.0 g of quercetin (9.9 mmol) were dissolved in 320 ml of ethanol, and 0.7 g of copper(II) chloride (5.2 mmol) was added. The reaction solution was stirred vigorously for 12 hours under the influence of oxygen. The reaction solution was evaporated to dryness in a rotary evaporator. 70 ml of hydrochloric acid (10% w/w) were added to the black oily residue. The beige solid which precipitated was filtered off with suction and dried at 40° C. in a vacuum drying cabinet.

Yield: 2.6 g of beige powder; 73% of theory $^{13}$C NMR data: (250 MHz) in DMSO δ (ppm): 14, 39, 58, 90, 95, 99, 106, 114, 116, 120, 124, 143, 145, 158, 163, 166, 195

$^1$H NMR data: (250 MHz) in DMSO δ (ppm): 0.9 (t, 3H), 3.15 (1H hidden), (1H hidden), 5.95 (s, 2H), 6.26 (s, 1OH), 6.51 (s, 1OH), 6.73 (d, 1H), 6.88 (dd, 1H), 7.05 (d, 1H), 9.87 (d, 2OH), 10.76 (s, 1OH), 11.35 (s, 1OH)

Mass spectrum: EI (m/e): 346 ($M^+$-$H_2O$)

UV Absorption Spectrum

The UV adsorption spectrum is illustrated in FIG. 1. Concentration: 1.2 mg/100 ml of methanol.

EXAMPLE 3

Preparation of 2-butoxy-2-(3,4-dihydroxyphenyl)-3,3,6,7-tetrahydroxychroman-4-one

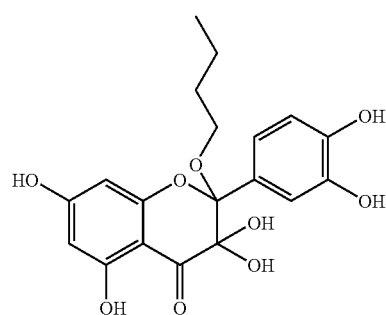

2.0 g of quercetin (6.6 mmol) and 0.45 g of copper(II) chloride (3.3 mmol) were suspended in 100 ml of 1-butanol. The suspension was stirred vigorously for 1 day at RT under the influence of oxygen.

The reaction solution was evaporated to dryness in a rotary evaporator. Hydrochloric acid (10% w/w) was added to the distillation residue. The aqueous phase was extracted with ethyl acetate and evaporated to dryness in a rotary evaporator.

The oily residue was purified by column chromatography.
Yield: 150 mg of yellow crystalline solid, 6% of theory
$^1$H NMR data: (250 MHz) in DMSO δ (ppm): 0.65 (m, 3H), 1.05 (m, 2H), 1.25 (m, 2H), 3.1 (m, 1H), 3.25 (m, 1H), 5.95 (s, 1H), 5.96 (s, 1H), 6.25 (s, 1OH), 6.51 (s, 1OH), 6.72 (d, 1H), 6.88 (dd, 1H), 7.05 (d, 1H), 8.86 (s, 1OH), 8.89 (s, 1OH), 10.75 (s, 1OH), 11.35 (s, 1OH)

Mass spectrum: ESI (m/e): 391 (M-H)$^-$

UV Adsorption Spectrum

The UV adsorption spectrum is illustrated in FIG. 2. Concentration: 1.7 mg/100 ml of methanol.

Assays

Determination of the Antiinflammatory Activity

Keratinocyte monolayer $PGE_2$ model. In order to induce inflammation, keratinocytes are incubated for 24 hours in 96-well plates (15,000 cells/well) with the pro-inflammatory substance (for example phorbol myristate acetate (PMA)). The preincubated cells (final concentration of PMA 0.1 μg/ml) are incubated for 24 hours with $10^{-6}$ M indometacin (positive control) or 0.2 mM of test substance. The negative control used is a control culture comprising no PMA. After incubation, the content of prostaglandin $E_2$ ($PGE_2$) in all three samples is determined by ELISA kits.

EXAMPLE 4

| | Lotion (W/O) for application to the skin | % by wt. |
|---|---|---|
| A | Polyglyceryl 2-dipolyhydroxystearate | 5.0 |
| | Beeswax | 0.5 |
| | Zinc stearate | 0.5 |
| | Hexyl laurate | 9.0 |
| | Cetyl isononanoate | 6.0 |
| | Shea butter | 0.5 |
| | DL-α-Tocopherol acetate | 1.0 |
| | 2-Butoxy-2-(3,4-dihydroxyphenyl)-3,3,5,7-tetrahydroxychroman-4-one | 0.5 |
| B | Glycerin | 5.0 |
| | Magnesium sulfate heptahydrate | 1.0 |
| | Preservatives | q.s. |
| | Water, demineralised | to 100 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The following are used as preservatives:

0.05% of propyl 4-hydroxybenzoate 0.15% of methyl 4-hydroxybenzoate

EXAMPLE 5

| | Lotion (W/O) for application to the skin | % by wt. |
|---|---|---|
| A | Polyglyceryl 2-dipolyhydroxystearate | 5.0 |
| | Beeswax | 0.5 |
| | Zinc stearate | 0.5 |
| | Hexyl laurate | 9.0 |
| | Cetyl isononanoate | 6.0 |
| | Shea butter | 0.5 |
| | DL-α-Tocopherol acetate | 1.0 |
| B | 2-Butoxy-2-(3,4-dihydroxyphenyl)-3,3,5,7-tetrahydroxychroman-4-one | 1.0 |
| | Glycerin | 5.0 |
| | Magnesium sulfate heptahydrate | 1.0 |
| | Preservatives | q.s. |
| | Water, demineralised | to 100 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The following are used as preservatives:

0.05% of propyl 4-hydroxybenzoate 0.15% of methyl 4-hydroxybenzoate

EXAMPLE 6

| | Lotion (W/O) for application to the skin | % by wt. |
|---|---|---|
| A | 4,6,3',4'-Tetrahydroxybenzyl-3-coumaranone | 1.0 |
| | 2-Butoxy-2-(3,4-dihydroxyphenyl)-3,3,5,7-tetrahydroxychroman-4-one | 1.0 |
| | Polyglyceryl 2-dipolyhydroxystearate | 5.0 |
| | Beeswax | 0.5 |
| | Zinc stearate | 0.5 |
| | Hexyl laurate | 9.0 |
| | Cetyl isononanoate | 6.0 |
| | Shea butter | 0.5 |
| | DL-α-Tocopherol acetate | 1.0 |
| B | Glycerin | 5.0 |
| | Magnesium sulfate heptahydrate | 1.0 |
| | Preservatives | q.s. |
| | Water, demineralised | to 100 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The following are used as preservatives:

0.05% of propyl 4-hydroxybenzoate 0.15% of methyl 4-hydroxybenzoate

EXAMPLE 7

A cream (O/W) comprising ectoine is prepared from the following components:

| | | | % by wt. |
|---|---|---|---|
| A | Paraffin, liquid | (1) | 8.0 |
| | Isopropyl myristate | (1) | 4.0 |
| | Mirasil CM5 | (2) | 3.0 |
| | Stearic acid | (1) | 3.0 |
| | Arlacel 165 V | (3) | 5.0 |
| | 2-Butoxy-2-(3,4-dihydroxyphenyl)-3,3,5,7-tetrahydroxychroman-4-one | | 1.0 |
| B | Glycerin (87%) | (1) | 3.0 |
| | Germaben II | (4) | 0.5 |
| | Water, demineralised | | to 100 |
| C | RonaCare ™ ectoine | (1) | 1.0 |

Preparation

Firstly, phases A and B are warmed separately to 75° C. Phase A is then slowly added to phase B with stirring, and stirring is continued until a homogeneous mixture has formed. After homogenisation of the emulsion, the mixture is cooled to 30° C. with stirring. The mixture is subsequently warmed to 35° C., phase C is added, and the mixture is stirred to homogeneity.

Sources of Supply (1) Merck KGaA (2) Rhodia (3) Uniqema (4) ISP

EXAMPLE 8

| | Topical composition as W/O emulsion | | |
|---|---|---|---|
| | | | % by wt. |
| A | Isolan PDI | (2) | 3.0 |
| | Paraffin oil, liq. | (1) | 17.0 |
| | Isopropyl myristate | | 5.0 |
| | Beeswax | | 0.2 |
| | Cutina HR | (2) | 0.3 |
| | 2-Butoxy-2-(3,4-dihydroxyphenyl)-3,3,5,7-tetrahydroxychroman-4-one | | 1.0 |
| B | Water, demineralised | | to 100 |
| | Glycerin (87%) | | 4.0 |
| | Magnesium sulfate | | 1.0 |
| | Germaben II-E | (3) | 1.0 |
| C | RonaCare ™ LPO | (1) | 2.0 |

Preparation

Phases A and B are warmed to 75° C. Phase B is added to phase A with stirring. The mixture is subsequently homogenised for 2 min. at 9000 rpm using the Turrax. The mixture obtained is cooled to 30 to 35° C., and C is stirred in.

Sources of Supply (1) Merck KGaA (2) Goldschmidt AG (3) ISP

Figure 1:
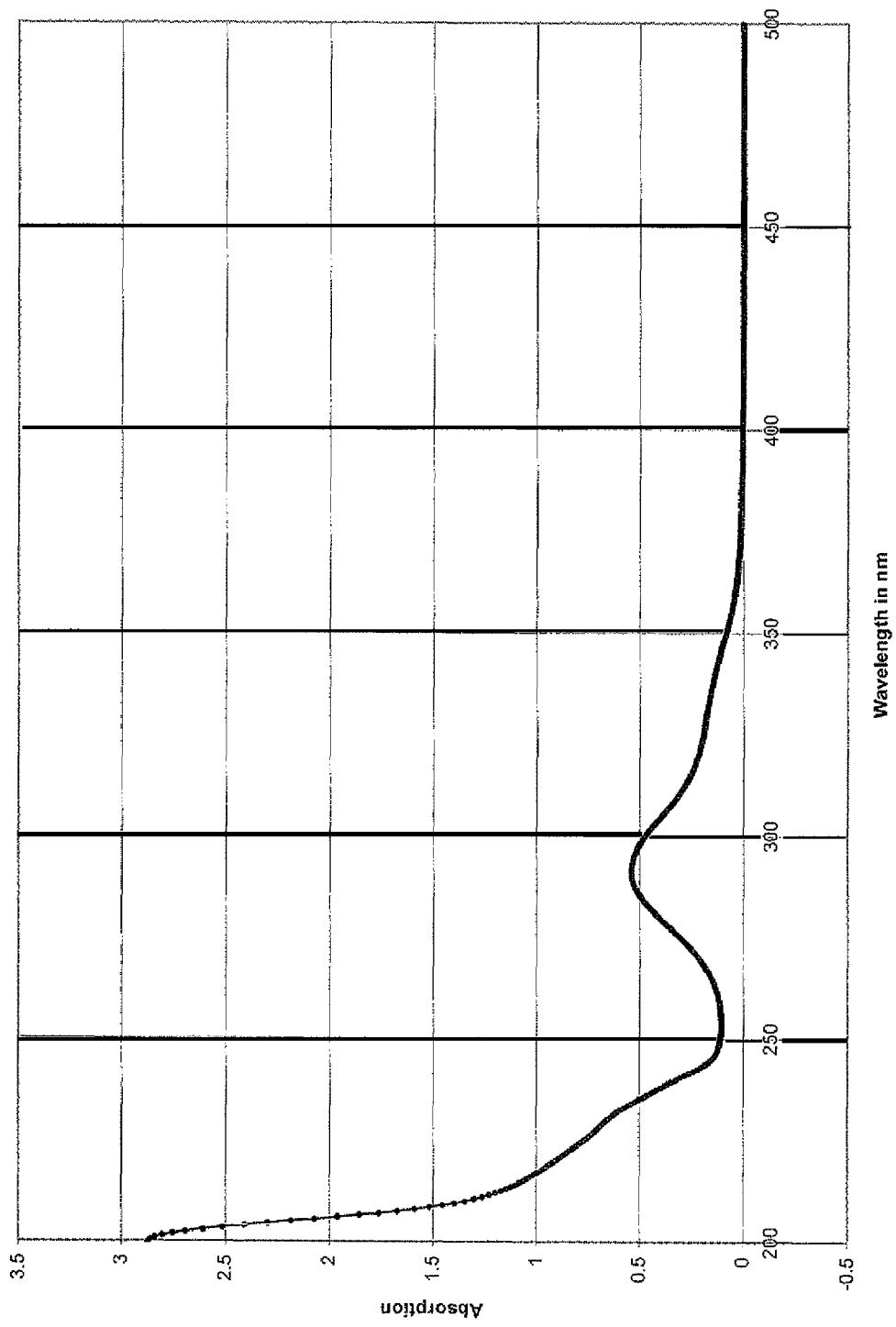
FIG. 1—illustrates the UV adsorption spectrum of the compound of example 2 in methanol.
Figure 2:
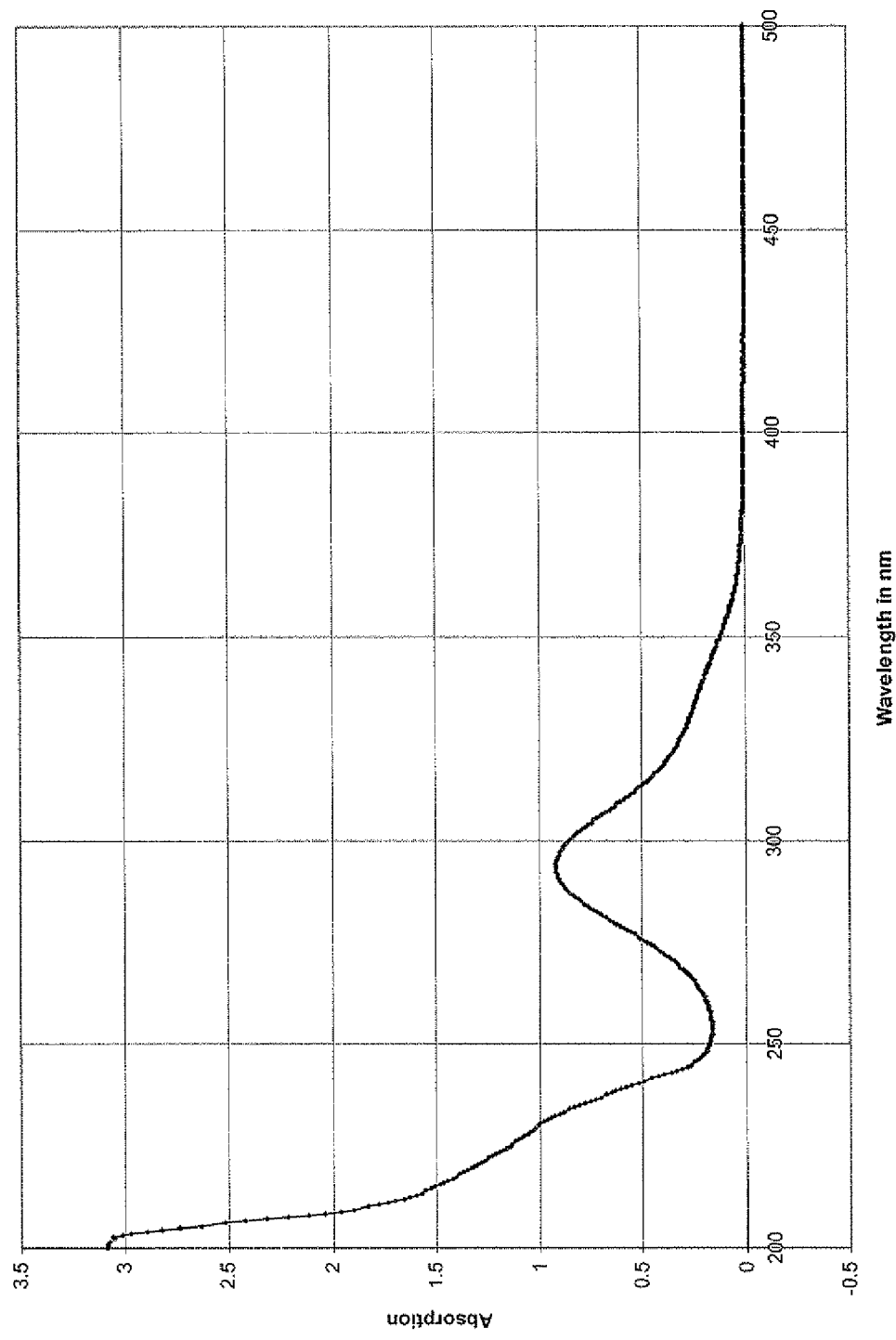
FIG. 2—illustrates the UV adsorption spectrum of the compound of example 3 in methanol.

The invention claimed is:

1. A composition suitable for topical application having antioxidative properties, comprising
   a) at least one compound of formula I

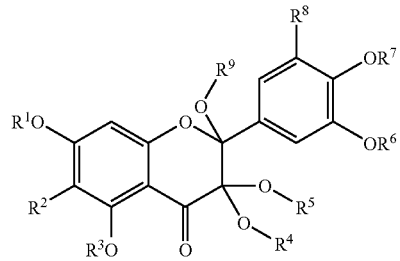

in which
$R^1$, $R^3$, $R^4$, $R^5$, $R^6$, $R^7$, $R^9$ are each, independently of one another, H or alkyl, and
$R^2$, $R^8$ are each, independently of one another, H, OH or —O-alkyl,
and
   b) a cosmetically suitable skin-tolerated vehicle, with the proviso that the skin-tolerated vehicle is not methanol, and
   c) optionally one or more further active compounds other than the compound of formula I having a skin-care and/or inflammation-inhibiting action.

2. A composition according to claim 1, wherein $R^1$, $R^3$, $R^4$, $R^5$, $R^6$, $R^7$, $R^9$ are each, independently of one another, H, branched or straight-chain $C_1$-$C_6$-alkyl, and $R^2$ and $R^8$, independently of one another, are H or OH.

3. A composition according to claim 1, wherein $R^4$=$R^5$.

4. A composition according to claim 3, wherein $R^1$ to $R^8$ are each H, and $R^9$ is H or $C_{1-6}$-alkyl.

5. A composition according to claim 1, comprising one or more further active compounds other than the compound of formula I having a skin-care and/or inflammation-inhibiting action.

6. A composition according to claim 1, which comprises one or more further antioxidant(s).

7. A composition according to claim 1, which further comprises one or more UV filters.

8. A composition according to claim 1, in which $R^9$ is branched or unbranched $C_3$-$C_{10}$-alkyl.

9. A composition according to claim 8, wherein $R^1$, $R^3$, $R^4$, $R^5$, $R^6$, $R^7$ are each, independently of one another, H, branched or unbranched $C_1$-$C_6$-alkyl, and $R^2$ and $R^8$, independently of one another, are H or OH.

10. A composition according to claim 9, wherein $R^1$ to $R^8$ are each H.

11. A composition according to claim 8, wherein $R^9$ is n-propyl, isopropyl, n-butyl, sec-butyl, tert-butyl, or n-pentyl.

12. A composition according to claim 1, wherein the compound of formula I is

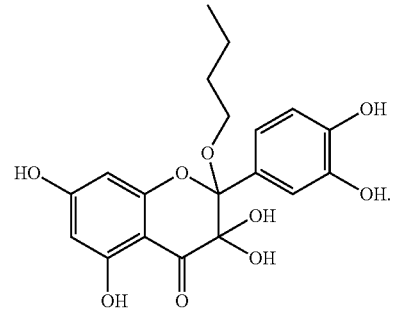

13. A composition according to claim 1, wherein the skin-tolerated vehicle is selected from the group consisting of vegetable oils, benzyl alcohols, alkylene glycols, polyethylene glycols, glycerol triacetate, gelatine, carbohydrates, lactose, starch, magnesium stearate, talc and Vaseline.

14. A composition according to claim 1, wherein the skin-tolerated vehicle is not ethanol.

* * * * *